(12) United States Patent
Ma et al.

(10) Patent No.: US 11,884,954 B2
(45) Date of Patent: Jan. 30, 2024

(54) **PROTEIN COMPLEX BASED ON DNA ENZYMES OF E FAMILY OF *ESCHERICHIA COLI* AND APPLICATION THEREOF IN ARTIFICIAL PROTEIN SCAFFOLDS**

(71) Applicant: Hubei University, Wuhan (CN)

(72) Inventors: Lixin Ma, Wuhan (CN); Chao Zhai, Wuhan (CN); Jun Yang, Wuhan (CN); Fei Wang, Wuhan (CN)

(73) Assignee: Hubel University, Wuhan (CN)

( * ) Notice: Subject to any disclaimer, the term of this patent is extended or adjusted under 35 U.S.C. 154(b) by 0 days.

(21) Appl. No.: 18/148,284

(22) Filed: Dec. 29, 2022

(65) Prior Publication Data
US 2023/0220439 A1    Jul. 13, 2023

Related U.S. Application Data

(63) Continuation of application No. PCT/CN2022/102567, filed on Jun. 30, 2022.

(30) Foreign Application Priority Data

Oct. 27, 2021    (CN) .......................... 202111256498.4

(51) Int. Cl.
| | |
|---|---|
| C12N 9/22 | (2006.01) |
| C12N 9/14 | (2006.01) |
| C12N 15/52 | (2006.01) |
| C07K 14/245 | (2006.01) |
| C12P 21/06 | (2006.01) |
| C12N 15/62 | (2006.01) |
| C12P 21/02 | (2006.01) |

(52) U.S. Cl.
CPC ............ *C12P 21/06* (2013.01); *C07K 14/245* (2013.01); *C12N 15/62* (2013.01); *C12P 21/02* (2013.01)

(58) Field of Classification Search
CPC . C12N 9/22; C12N 19/14; C12N 9/42; C12N 15/70; C12N 15/52; C07K 14/245; C12Y 302/01091
See application file for complete search history.

(56) References Cited

U.S. PATENT DOCUMENTS

2016/0186156 A1    6/2016  Bayer et al.

FOREIGN PATENT DOCUMENTS

WO    2017100584 A1    6/2017

OTHER PUBLICATIONS

Wei Li et al., "Dual Recognition and the Role of Specificity-Determining Residues in Colicin E9 DNase-Immunity Protein Interactions", Biochemistry. 1998, pp. 11771-11779, vol. 37, No. 34.
Anthony H. Keeble et al., "The Kinetic Basis for Dual Recognition in Colicin Endonuclease-Immunity Protein Complexes", Journal of Molecular Biology, 2005, pp. 656-671, vol. 352, No. 3.
Hiroyuki Inoue et al., "Contribution of a family 1 carbohydrate-binding module in thermostable glycoside hydrolase 10 xylanase from Talaromyces cellulolyticus toward synergistic enzymatic hydrolysis of lignocellulose", Biotechnology for Biofuels, 2015, pp. 1-13, vol. 8, No. 77.
Yihan Liu et al., "Studies on properties of the xylan-binding domain and linker sequence of xylanase XynG1-1 from Paenibacillus campinasensis G1-1", J Ind Microbiol Biotechnol, 2015, pp. 1591-1599, vol. 42, No. 12.
Youzhi Miao et al., "Effect of CBM1 and linker region on enzymatic properties of a novel thermostable dimeric GH10 xylanase (Xyn10A) from filamentous fungus *Aspergillus fumigatus* Z5", AMB Express, 2018, pp. 1-10, vol. 8, No. 44.
Haruhiko Sakuraba et al., "Structure of L-aspartate oxidase from the hyperthermophilic archaeon Sulfolobus tokodaii", Biochim Biophys Acta, 2008, pp. 563-571, vol. 1784, No. 3.
Matthew A. Smith et al., "A diverse set of family 48 bacterial glycoside hydrolase cellulases created by structure-guided recombination", FEBS Journal, 2012, pp. 4453-4465, vol. 279, No. 24.
Michael Anbar et al., "Improved Thermostability of Clostridium thermocellum Endoglucanase Cel8A by Using Consensus-Guided Mutagenesis", Applied and Environmental Microbiology, 2012, pp. 3458-3464, vol. 78, No. 9.
Igor A. Dvortsova et al., "Carbohydrate binding module CBM28 of endoglucanase Cel5D from Caldicellulosiruptor bescii recognizes crystalline cellulose", Int. J. Bio. Macromol, 2017, pp. 305-311, vol. 107.
Xiaowei Peng et al., "A multifunctional thermophilic glycoside hydrolase from Caldicellulosiruptor owensensis with potential applications in production of biofuels and biochemicals", Biotechnology for Biofuels, 2016, pp. 1-13, vol. 9, No. 98.
CNIPA, Notification of a First Office Action for CN202111256498. 4, dated Jun. 29, 2022.
Hubei University (Applicant), Reply to Notification of a First Office Action for CN202111256498.4, w/ replacement claims, Aug. 11, 2022.

(Continued)

*Primary Examiner* — Maryam Monshipouri
(74) *Attorney, Agent, or Firm* — Zhigang Ma (57) ABSTRACT

A protein complex based on DNA enzymes of an E family of *Escherichia coli* and an application thereof in artificial protein scaffolds are provided. The protein complex includes one or more of interaction pairs formed by a CL2 protein and an Im2 protein, a CL7 protein and an Im7 protein, a CL8 protein and an Im8 protein, or a CL9 protein and an Im9 protein. By protein engineering of a carboxyl terminus DNase domain of the DNA enzymes CE2, CE7, CE8 and CE9, mutants that lose DNA enzyme activity but still retain the ultra-high affinity with the corresponding Im protein are obtained, and protein interaction pairs CL2/Im2, CL7/Im7, CL8/Im8 and CL9/Im9 are constructed. These protein interaction pairs have properties of heat resistance, high affinity, high specificity, small molecular weight, fast assembly speed, etc. Based on this, an artificial protein scaffold is constructed for the construction of artificial multienzyme complexes.

3 Claims, 3 Drawing Sheets

Specification includes a Sequence Listing.

(56) References Cited

OTHER PUBLICATIONS

Hubei University (Applicant), Supplemental Reply to Notification of a First Office Action for CN202111256498.4, w/ replacement claims, Aug. 16, 2022.
Hubei University (Applicant), Supplemental Reply to Notification of a First Office Action for CN202111256498.4, w/ (allowed) replacement claims, Aug. 23, 2022.
CNIPA, Notification to grant patent right for invention in CN202111256498.4, dated Sep. 8, 2022.

PROTEIN COMPLEX BASED ON DNA ENZYMES OF E FAMILY OF *ESCHERICHIA COLI* AND APPLICATION THEREOF IN ARTIFICIAL PROTEIN SCAFFOLDS

TECHNICAL FIELD

The disclosure relates to the field of synthetic biology and nanobiotechnologies, and more particularly to a protein complex based on DNA enzymes of an E family of *Escherichia coli* and an application/use thereof in artificial protein scaffolds.

STATEMENT REGARDING SEQUENCE LISTING

The sequence listing associated with this application is provided in text format in lieu of a paper copy and is hereby incorporated by reference into the specification. The name of the XML file containing the sequence listing is 22015JHG-USP1-ZL224926-USP1-SL.xml. The XML file is 16,980 bytes; is created on Dec. 5, 2022; and is being submitted electronically via EFS-Web.

BACKGROUND

Protein interaction pairs with high affinity have been widely used in many fields, such as co-immunoprecipitation, protein pull down assay, yeast two-hybrid and enzyme immobilization. Among them, a multienzyme complex system formed by self-assembly of protein interaction pairs has attracted much attention because of its excellent synergistic catalytic ability. For one-pot synthesis reactions, multiple enzyme molecules are assembled in a specific order by using multiple orthogonal protein interaction pairs, and the cascade catalytic reaction is carried out in the form of artificial multienzyme complexes, which is conducive to the formation of substrate channels, preventing the diffusion of intermediate products, promoting the timely conversion of the intermediate products, so as to avoid the interference of some toxic intermediates on enzyme activity and improve the reaction efficiency. At present, the protein-protein interaction is mainly realized by a basic assembly element Cohesin-Dockerin from cellulosome and the artificially designed SpyCatcher/SpyTag, SnoopCatcher/SnoopTag, RIAD/RIDD and other protein interactions. However, the existing protein interaction pairs have many problems in practical applications. First of all, the number of strong interaction pairs is limited, the affinity of commonly used interaction pairs is not strong, and thus the structure is unstable and easy to collapse when constructing more complex multienzyme complexes. Secondly, for some exothermic reactions, such as cellulose degradation, thermostable protein interaction pairs are required to combine with thermostable enzymes to construct multienzyme complexes, and such protein-protein interaction pairs are even fewer at present. In addition, most protein interaction pairs need to interact under high salt ions, such as Cohesin-Dockerin, which is regulated by calcium ions, limiting their application in vivo. Therefore, it is of great significance to find new protein interaction pairs with excellent properties for the above problems.

Colistin produced by *Escherichia coli* is a cytotoxin, which can kill bacilli with relatively close relatives. DNA enzymes (also referred to as deoxyribonuclease abbreviated as DNase) of the E family of colistin, including colicin E2 DNase (CE2), colicin E7 DNase (CE7), colicin E8 DNase (CE8) and colicin E9 DNase (CE9), are a kind of non-specific endonucleases with highly similar structures. In host cells, CE proteins (e.g., CE2, CE7, CE8, and CE9) bind to their corresponding immunity proteins immunity 2 (Im2), Im7, Im8 and Im9, inhibiting the binding of the CE proteins to DNA, thereby eliminating their toxicity to the host. The binding of the CE protein and the Im protein is one of the strongest protein interactions known in nature, with $K_d$ reaching $10^{-14} \sim 10^{-17}$. The binding of the Im protein and the CE protein is a "dual-recognition mechanism", that is, the Im protein first forms a sequence-independent complex with the CE nuclease through a conservative element (helix III), and then the helix II containing specific residues on the Im protein combines with the corresponding CE nuclease to stabilize the orthogonal complex (Wei Li et al., "Dual Recognition and the Role of Specificity-Determining Residues in Colicin E9 DNase-Immunity Protein Interactions", Biochemistry. 1998, pages 11771-11779, Vol. 37, No. 34; Anthony H. Keeble et al., "The Kinetic Basis for Dual Recognition in Colicin Endonuclease-Immunity Protein Complexes", Journal of Molecular Biology, 2005, pages 656-671, Vol. 352, No. 3).

SUMMARY

Purposes of the disclosure are to provide a protein complex based on DNA enzymes of an E family of *Escherichia coli* and an application thereof in an artificial protein scaffold. By protein engineering of the carboxyl terminus DNase domain of DNA enzymes colicin E2 DNase (CE2), CE7, CE8 and CE9 of the CE family (i.e., the E family of colistin), the disclosure obtains mutants (including CL2, CL7, CL8, and CL9) that lose DNA enzyme activity but still retain the ultra-high affinity with the corresponding Im protein, and protein interaction pairs including CL2/Im2, CL7/Im7, CL8/Im8 and CL9/Im9 are constructed. It is found that the protein interaction pairs have the properties of heat resistance, high affinity, high specificity, small molecular weight, fast assembly speed, etc. Based on this, an artificial protein scaffold is constructed, which provides a new platform for the construction of artificial multienzyme complexes.

In a first aspect, the disclosure provides a protein complex based on DNA enzymes of an E family of *Escherichia coli*. The protein complex includes: one or more selected from the group consisting of an interaction pair formed by a CL2 protein and an immunity (Im2) protein, an interaction pair formed by a CL7 protein and an Im7 protein, an interaction pair formed by a CL8 protein and an Im8 protein, and an interaction pair formed by a CL9 protein and an Im9 protein;

an amino acid sequence of the CL2 protein is shown in SEQ ID NO: 2;
 an amino acid sequence of the CL7 protein is shown in SEQ ID NO: 5;
 an amino acid sequence of the CL8 protein is shown in SEQ ID NO: 8; and
 an amino acid sequence of the CL9 protein is shown in SEQ ID NO: 11.
 Specifically,
 an amino acid sequence of the Im2 protein is shown in SEQ ID NO: 3;
 an amino acid sequence of the Im7 protein is shown in SEQ ID NO: 6;
 an amino acid sequence of the Im8 protein is shown in SEQ ID NO: 9; and
 an amino acid sequence of the Im9 protein is shown in SEQ ID NO: 12.

Specifically,
the CL2 protein is obtained by mutation based on the CE2 protein as shown in SEQ ID NO: 1;
the CL7 protein is obtained by mutation based on the CE7 protein as shown in SEQ ID NO: 4;
the CL8 protein is obtained by mutation based on the CE8 protein as shown in SEQ ID NO: 7; and
the CL9 protein is obtained by mutation based on the CE9 protein as shown in SEQ ID NO: 10.

In a second aspect, the disclosure provides an application of the protein complex in preparing an artificial protein scaffold.

In a third aspect, the disclosure provides a scaffold protein based on the protein complex, the scaffold protein includes: a carbohydrate-binding module 3a (CBM3a, also referred to as cellulose-binding module), the Im2 protein, the Im7 protein, the Im8 protein and the Im9 protein in series through linkers.

Each of the cellulose-binding module CBM3a, the Im2 protein, the Im7 protein, the Im8 protein and the Im9 protein on the scaffold protein is capable of being connected to a corresponding CL protein to form an interaction pair, and target proteins are connected to the CL proteins to realize an orderly assembly of the target proteins on the scaffold protein.

In an embodiment, the cellulose-binding module CBM3a is derived from *Clostridium thermopellum*.

In an embodiment, the linkers include: a first linker (also referred to as Linker 1) for connecting the CBM3a and the Im2 protein with an amino acid sequence of TTTTTTTAT-TASSTSTTSTSATSG shown in SEQ ID NO: 13, a second linker (also referred to as Linker 2) for connecting the Im2 protein and the Im7 protein with an amino acid sequence of NTLTIGGGGGGGGTNPGT shown in SEQ ID NO: 14, a third linker (also referred to as Linker 3) for connecting the Im7 protein and the Im8 protein with an amino acid sequence of GASGSGTTTTTTTTTTTTTTGGGTDP shown in SEQ ID NO: 15, and a fourth linker (also referred to as Linker 4) for connecting the Im8 protein and the Im9 protein with an amino acid sequence of SSWEGISTDDG-IVHSVRISGNKTLS shown in SEQ ID NO: 16.

In a fourth aspect, the disclosure is to provide a method for constructing the scaffold protein, including:
step 1, acquiring gene fragments of the CBM3a, the Im2 protein, the Im7 protein, the Im8 protein and the Im9 protein by polymerase chain reaction (PCR) amplification;
step 2, connect the gene fragments of the CBM3a, the Im2 protein, the Im7 protein, the Im8 protein and the Im9 protein obtained in the step 1 sequentially in that order by using overlapping PCR technology; and
step 3, constructing a recombinant vector of connected gene in the step 2, introducing the recombinant vector into a receptor cell, and inducing expression to obtain the scaffold protein.

In a fifth aspect, the disclosure provides an application of the scaffold protein in preparing a multienzyme complex system.

In a sixth aspect, the disclosure provides a multienzyme complex system based on the scaffold protein. The multienzyme complex system includes: four CL-tagged cellulases and the scaffold protein mentioned above, the four CL-tagged cellulases and the corresponding Im proteins on the scaffold protein are connected to form interaction pairs to obtain the multienzyme complex.

The four CL-tagged cellulases include: an exoglucanase connected with the CL2 protein, an endoglucanase mutant connected with the CL7 protein, an endoglucanase connected with the CL8 protein, and a beta-glucosidase connected with the CL9 protein.

In an embodiment, the exoglucanase is an exoglucanase Cel48S$_{m3}$ obtained by DNA shuffling, the endoglucanase mutant is an endoglucanase mutant Cel8A* (K276R, G283P, S329G, S375T) derived from *Clostridium thermocellum*, the endoglucanase connected with the CL8 protein is an endoglucanase GH5D derived from *Caldicellulosiruptor bescii*, and the beta-glucosidase is a beta-glucosidase CoGH1A derived from *Caldicellulosiruptor owensensis*.

In a seventh aspect, the disclosure provides an application of the multienzyme complex system in hydrolyzing a cellulose substrate.

Compared with the prior art, beneficial effects of the disclosure are as follows. In the disclosure, the protein complex based on the DNA enzymes of the E family of *Escherichia coli* and the application thereof in the artificial protein scaffold are provided. By the protein engineering of the carboxyl terminus DNase domain of the DNA enzymes CE2, CE7, CE8 and CE9 of the CE family, the disclosure obtains mutants including CL2, CL7, CL8, and CL9 that lose DNA enzyme activity but still retain the ultra-high affinity with the corresponding Im protein, and protein interaction pairs including CL2/Im2, CL7/Im7, CL8/Im8 and CL9/Im9 are constructed. It is found that the toolbox of the CL/Im protein interaction pairs has characteristics of high specificity, ultra-high affinity, high thermal stability, and structural unity, and thus a stable and heat-resistant protein scaffold and a platform for multienzyme assembly carried out according to a set order can be constructed based on the CL/Im toolbox, providing a basis for building a highly robust multienzyme molecular machine. In the disclosure, the four cellulases are assembled on the artificial protein scaffold to form the multienzyme complex, which can hydrolyze the cellulose substrate more efficiently under a high-temperature environment. In addition, the above protein interaction pairs can be used in any field involving protein-protein interaction.

DETAILED DESCRIPTION OF EMBODIMENTS

Technical solutions of the disclosure will be described clearly and completely in combination with embodiments of the disclosure. Apparently, the described embodiments are only part of the embodiments of the disclosure, not all of them. Based on the embodiments of the disclosure, all other embodiments obtained by those skilled in the art without creative labor are within the protection scope of the disclosure.

Embodiment 1 Expression and Purification of CL Proteins and Immunity (Im) Proteins 1. Through amino acid sequence comparison with CL7 protein, based on the high similarity of four protein sequences, the carboxyl terminus DNase domain of DNA enzymes colicin E2 DNase (CE2), CE7, CE8 and CE9 of CE family (i.e., the E family of colistin) is performed with protein engineering to obtain mutants CL2, CL7, CL8 and CL9 that lose DNA enzyme activity but still retain the ultra-high affinity with the corresponding Im protein. The sequences of four groups of CL-Im and four wild type CE proteins are:

(1) an amino sequence of the CE2 protein as shown in SEQ ID NO: 1, an amino sequence of the CL2 protein as shown in SEQ ID NO: 2, and an amino sequence of the Im2 protein as shown in SEQ ID NO: 3;

(2) an amino sequence of the CE7 protein as shown in SEQ ID NO: 4, an amino sequence of the CL7 protein as shown in SEQ ID NO: 5, and an amino sequence of the Im7 protein as shown in SEQ ID NO: 6;

(3) an amino sequence of the CE8 protein as shown in SEQ ID NO: 7, an amino sequence of the CL8 protein as shown in SEQ ID NO: 8, and an amino sequence of the Im8 protein as shown in SEQ ID NO: 9; and (4) an amino sequence of the CE9 protein as shown in SEQ ID NO: 10, an amino sequence of the CL9 protein as shown in SEQ ID NO: 11, and an amino sequence of the Im9 protein as shown in SEQ ID NO: 12.

2. Genes of all mutants and Im proteins are synthesized by Wuhan GeneCreate Biological Engineering Co., Ltd. of China, and coding genes of the four CL proteins and the four Im proteins are respectively constructed into pET23a vector by conventional methods in the related art. The recombinant plasmid is transferred into *Escherichia coli* BL21(DE3), induced for expression and purified. Specifically, the expression strain is inoculated into liquid lysogeny broth (LB) medium supplemented with 100 micrograms per liter (μg/mL) ampicillin, and cultured overnight at 37° C. Then, the seed liquid is inoculated into a terrific broth (TB) medium at a volume ratio of 1:100, and when the optical density 600 (OD600) value reached 0.8~1.0, isopropyl-β-D-thiogalactoside (IPTG) with a final concentration of 1 millimole per liter (mM) is added and induced at 18° C. and 220 revolutions per minute (rpm) for 16-18 hours; The thalli are collected, fully resuspended with tris-buffered saline (TBS) buffer (pH 7.4), and repeatedly disrupted for 5 times with a high-pressure cell disruptor, and then centrifuged with a 10000 at rpm for 30 minutes, and the supernatant is transferred to the pretreated gravity column.

Figure 1:
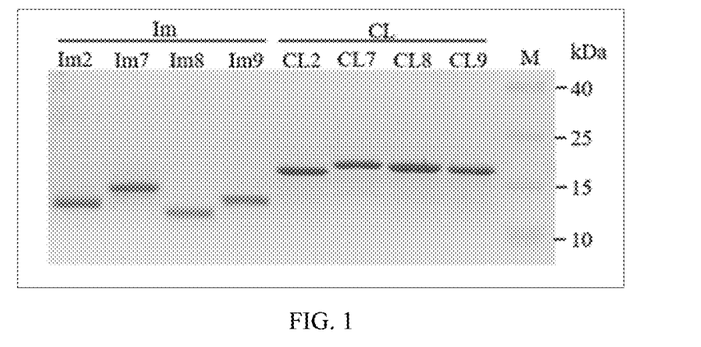
FIG. 1 illustrates a schematic diagram of four CL proteins and four Im proteins after purification detected by sodium dodecyl sulfate-polyacrylamide gel electrophoresis (SDS-PAGE) assay according to an embodiment 1 of the disclosure.

The pretreatment method is as follows. 4 milliliters (mL) of nickel beads are absorbed into 60 mL of protein purification gravity column, and balanced with 3 times the column volume of bacteria-cracking buffer. The supernatant is transferred to the gravity column, sealed with a parafilm, incubated at 4° C. for 1 hour in a silent mixer, and then washed with 3 times the column volume of TBS (containing 10 mM imidazole) for 3 times. Subsequently, the column is successively washed with TBS containing 30 mM, 50 mM, and 200 mM three times in each case 3 times the column volume, and the effluents are collected separately. The collected solution eluted by each gradient of imidazole is detected by sodium dodecyl sulfate-polyacrylamide gel electrophoresis (SDS-PAGE) assay. The results are shown in FIG. 1, indicating that all CL and Im proteins can be successfully expressed and purified. The recombinant protein samples are ultra-filtrated and concentrated, and then sub-packaged and stored at −80° C.

Embodiment 2 Native-Polyacrylamide Gel Electrophoresis (PAGE)

1. Preparation of Native Polyacrylamide Gel of Native-PAGE

For the verification of the binding specificity of CL-Im protein interaction pairs, 30% acrylamide (37.5:1) and glycerol electrophoresis system are used, and the specific formula is shown in Table 1.

TABLE 1

Formula of native polyacrylamide gel of Native-PAGE

| Separation gel | | Concentrated gel | |
|---|---|---|---|
| Component | Volume (mL) | Component | Volume (mL) |
| 37.5:1 acrylamide | 1.6 | 37.5:1 acrylamide | 0.83 |
| 1.5M Tris-HCl pH 8.8 | 1 | 1M Tris-HCl pH 6.8 | 0.63 |
| 60% glycerol | 0.587 | 60% glycerol | — |
| 10% APS | 0.015 | 10% APS | 0.050 |
| TEMED | 0.004 | TEMED | 0.005 |
| ddH$_2$O | 0.794 | ddH$_2$O | 3.45 |
| Total volume | 4 | Total volume | 5 |

2. Native-PAGE

Figure 2A:
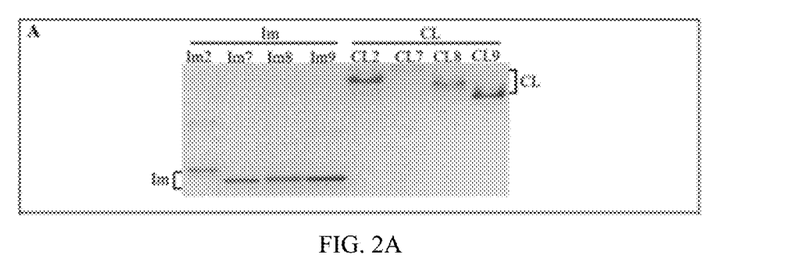
FIG. 2A illustrates a schematic diagram of the four CL proteins and the four Im proteins after purification detected by Native PAGE assay according to an embodiment 2 of the disclosure.
Figure 2B:
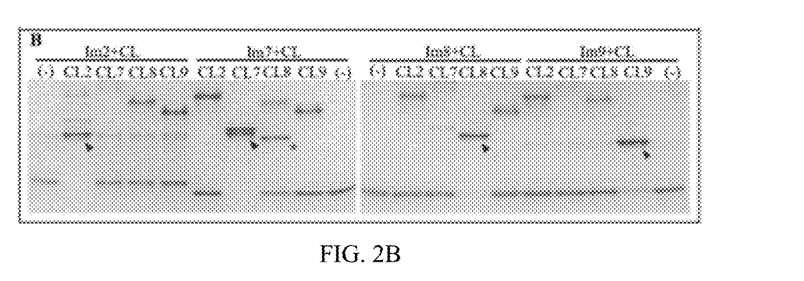
FIG. 2B illustrates protein interactions between the four CL proteins and the four Im proteins according to the embodiment 2 of the disclosure.

In order to verify the specificity of the bonding of the CL proteins and the Im proteins, in this embodiment, the four CL proteins and the four Im proteins are mixed respectively to obtain 16 combinations, which are incubated at room temperature for 30 minutes and then subjected to Native-PAGE, with a voltage of 120 Volts (V) for the upper gel and 180 V for the lower gel. When the bromophenol blue indicator band moves to a bottom of the gel, electrophoresis is terminated, and then staining is performed. The electrophoretic results are shown in FIG. 2B, indicating that the interactions between CL and Im proteins have good specificity.

Figure 2C:
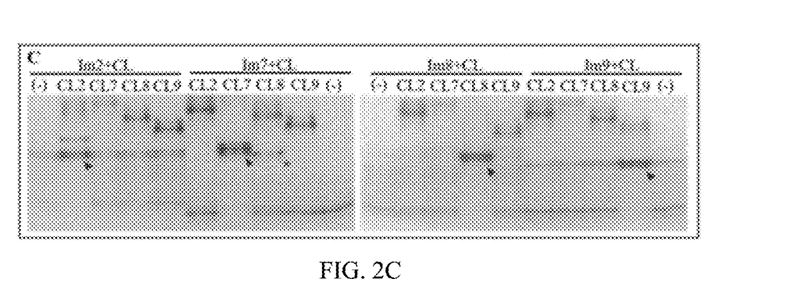
FIG. 2C illustrates heat resistance of the protein interactions between the four CL proteins and the four Im proteins according to the embodiment 2 of the disclosure.

To further verify the thermal stability of the binding of CL and Im proteins, specifically, the 16 combinations of the CL-Im protein mixed systems are incubated at room temperature for 30 minutes, heated in 100° C. water bath for 1 hour respectively, and the Native-PAGE is performed on the protein mixed samples after high-temperature treatment. The test results are shown in FIG. 2C, showing that the structures of Im and CL proteins change slightly after high-temperature treatment, resulting in the blurring of active gel protein bands, but the four groups of Im-CL complexes formed by orthogonal each other do not change significantly under high-temperature environment, which indicates that the interactions between Im and CL proteins have good thermal stability.

Embodiment 3 Construction of Scaffold Protein Scaf-CIQ and Verification of its Thermal Stability 1. In this embodiment, the corresponding scaffold protein is constructed based on the interaction pairs formed by the combination of the CL and Im proteins, as follows.

Figure 3:
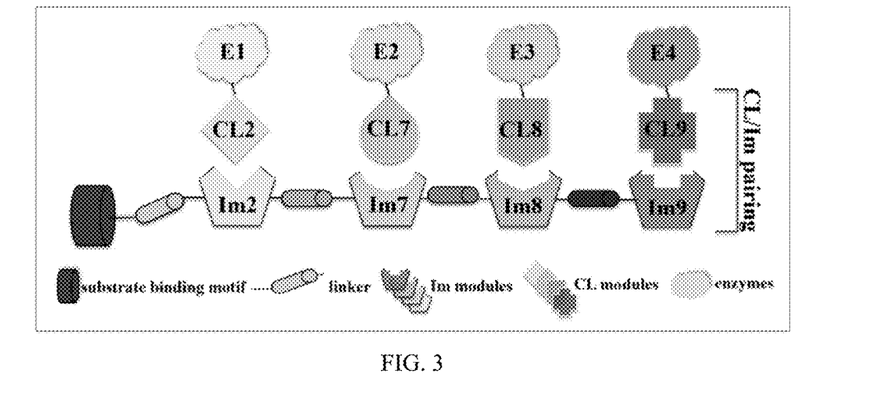
FIG. 3 illustrates a schematic diagram of a principle of a multienzyme complex assembled by a scaffold protein according to an embodiment 3 of the disclosure.

Scaf-CIQ, a scaffold protein in CIQ system, is a carbohydrate-binding module 3a (CBM3a, also referred to as a cellulose-binding module) derived from *Clostridium thermocellum* (living environment is 60~90° C.), and is a fusion protein expressed in series with Im2, Im7, Im8 and Im9 through linkers. The presence of CBM3a endows the scaffold protein Scaf-CIQ with the ability to combine with cellulose matrices such as microcrystalline cellulose (Avicel) and phosphoric acid swollen cellulose (PASC), thus achieving the purpose of targeting cellulose matrices and immobilize enzymes. The principle of the scaffold protein Scaf-CIQ is shown in FIG. 3, each Im module (also referred to as the Im protein) on the scaffold protein Scaf-CIQ can only be combined with a target protein including the corresponding CL-tag, such as an enzyme, so that the ordered assembly of four target proteins on the scaffold protein Scaf-CIQ is realized, and the assembled complex is named multiple complexes-CL-Im quartet (MEC-CIQ).

The construction process of the scaffold protein is as follows.

Corresponding gene fragments of the four kinds of Im proteins and the CBM3a are obtained by polymerase chain reaction (PCR) amplification, integrated by overlapping PCR technology to obtain gene sequences containing 1-4 Im modules, and recombinant vectors are constructed. Specifically, the vector skeleton selected for the scaffold protein is pET23a vector subjected to double enzyme digestion by NdeI and XhoI. When primers are designed, the forward primer of CBM3a gene contains 15 nucleotides which are homologous with a flanking sequence of the NdeI site of the pET23a vector, and the coding sequences of Im2, Im7, Im8 and Im9 respectively each carry a recombination sequence that is homologous with 15 bases of a flanking sequence of the XhoI site of the pET23a vector according to the different number of Im modules.

Specifically, the CBM3a and the Im2 protein are connected by a first linker (also referred to as Linker 1) with an amino acid sequence of TTTTTTTATTASSTSTTSTSATSG shown in SEQ ID NO: 13 (Hiroyuki Inoue et al., "Contribution of a family 1 carbohydrate-binding module in thermostable glycoside hydrolase 10 xylanase from *Talaromyces cellulolyticus* toward synergistic enzymatic hydrolysis of lignocellulose", Biotechnology for Biofuels, 2015, pages 1-13, Vol. 8, No. 77.), the Im2 protein and the Im7 protein are connected by a second linker (also referred to as Linker 2) with an amino acid sequence of NTLTIGGGGGGGGTNPGT shown in SEQ ID NO: 14 (Yihan Liu et al., "Studies on properties of the xylan-binding domain and linker sequence of xylanase XynG1-1 from *Paenibacillus campinasensis* G1-1", J Ind Microbiol Biotechnol, 2015, pages 1591-1599, Vol. 42, No. 12.), the Im7 protein and the Im8 protein are connected by a third linker (also referred to as Linker 3) with an amino acid sequence of GASGSGTTTTTTTTTTTTTGGGTDP shown in SEQ ID NO: 15 (Youzhi Miao et al., "Effect of CBM1 and linker region on enzymatic properties of a novel thermostable dimeric GH10 xylanase (Xyn10A) from filamentous fungus *Aspergillus fumigatus* Z5", AMB Express, 2018, pages 1-10, Vol. 8, No. 44.), and the Im8 protein and the Im9 protein are connected by a fourth linker (also referred to as Linker 4) with an amino acid sequence of SSWEGISTDDGIVHSVRISGNKTLS shown in SEQ ID NO: 16 (Haruhiko Sakuraba et al., "Structure of L-aspartate oxidase from the hyperthermophilic archaeon *Sulfolobus tokodaii*", Biochim Biophys Acta, 2008, pages 563-571, Vol. 1784, No. 3.).

The gene fragments of the four kinds of Im proteins with different Linker sequences and CBM3a are amplified by PCR. CBM3a, Im2 (Im2+Im7, Im2+Im7+Im8, Im2+Im7+Im8+Im9) are mixed with the linearized pET23a linear vector at a molar ratio of 3:1 to obtain a mixed system, 0.5 U T5 nucleic acid exonuclease and corresponding New England Biolabs (NEB) Buffer™ 4 are added into the 5 μL of the mixed system. After *Escherichia coli* DH5α competent cells are added, it is allowed to stand on an ice-water mixed bath for 5 minutes, the homologous arm region of the gene will produce a 3'-protruding cohesive end. After the gene fragments are transferred into the competent cell, circular vectors containing complete genetic sequences of 1-4 Im modules and CBM3a is obtained by homologous recombination in *Escherichia coli*, in which the scaffold protein containing only one Im2 module is named Scaf-CIM, the scaffold protein containing both Im2 and Im7 modules is named Scaf-CIB, the scaffold protein containing Im2, Im7 and Im8 modules is named Scaf-CIT, and the scaffold protein containing Im2, Im7, Im8 and Im9 modules is named Scaf-CIQ.

Figure 4:
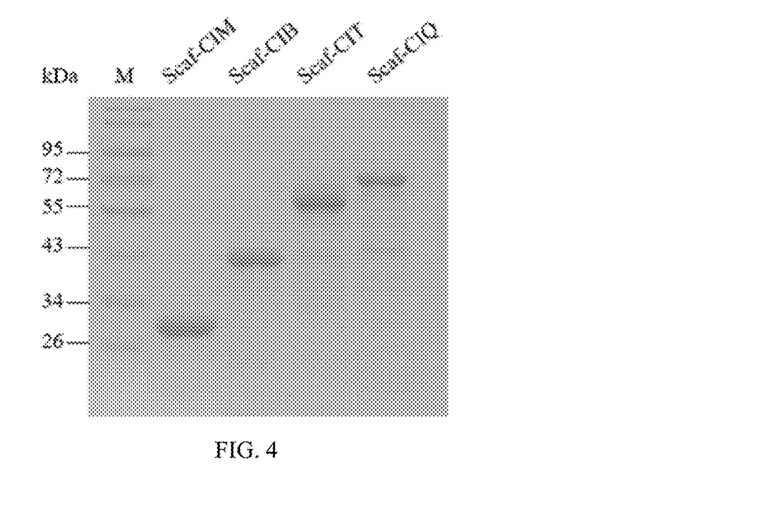
FIG. 4 illustrates a schematic diagram of the scaffold protein containing 1-4 Im modules after purification detected by the SDS-PAGE assay according to the embodiment 3 of the disclosure.

The recombinant vectors are transferred into *Escherichia coli* BL21 (DE3) for induction and expression, and then purified by Ni-NTA method, and the purified proteins are detected. The detection results are shown in FIG. 4. SDS-PAGE results show that the scaffold proteins containing CBM3a and 1-4 Im modules could be purified by the Ni-NTA method to obtain highly purified proteins.

2. To investigate the thermal stability of the scaffold protein Scaf-CIQ, the following methods are used.

A carboxyl terminus of the scaffold protein Scaf-CIQ is Im9, and an amino terminus is CBM3a. It is known that Im9 is specifically bound to CL9, and CBM3a can be bound to phosphoric acid swollen cellulose. Based on this, when exploring the thermal stability of the scaffold protein Scaf-CIQ, the phosphoric acid swollen cellulose is used as the immobilization matrix, and the green fluorescence could be displayed on the phosphoric acid swollen cellulose ix) through the combination of Im9 and sfGFP fused with CL9-tag (CL9-sfGFP) at the amino end. According to the intensity of green fluorescence, the integrity of the scaffold protein Scaf-CIQ can be judged, that is, whether the scaffold protein Scaf-CIQ retains the function of CBM3a at the amino terminus and Im9 at the carboxyl terminus after high-temperature treatment.

Figure 5:
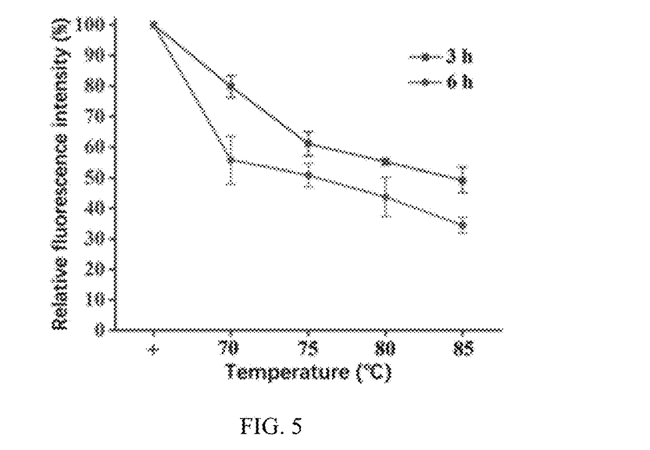
FIG. 5 illustrates thermal stability test results of the scaffold protein Scaf-CIQ according to the embodiment 3 of the disclosure.

In this embodiment, the scaffold protein Scaf-CIQ is incubated at 70° C., 75° C., 80° C. and 85° C. for 3 hours and 6 hours respectively, centrifuged at 12000 rpm for 5 minutes, the supernatant is mixed with the phosphoric acid swollen cellulose and added with excess CL9-sfGFP is added, incubated at 220 rpm at 28° C. for 1 hour. Then, the phosphoric acid swollen cellulose is washed with 2 M NaCl three times to remove free proteins, the samples are resuspended in 100 μL TBS buffer, and the fluorescence intensity of CL9-sfGFP in each sample is quantified by fluorescence spectrophotometer. The fluorescence intensity measured by combining untreated Scaf-CIQ with CL9-sfGFP and phosphoric acid swollen cellulose is 100%, and the sample without Scaf-CIQ is used as a negative control. The detection results of relative fluorescence intensity are shown in FIG. 5. The results show that the scaffold protein Scaf-CIQ has a binding capacity of about 50% to cellulose and CL9-sfGFP after 3 hours of culture at 85° C., and still has a binding capacity of more than 30% after 6 hours, which means that the scaffold protein Scaf-CIQ of the disclosure has high thermal stability, and thus the scaffold protein Scaf-CIQ can be applied to the assembly and application of multienzyme complexes under high-temperature environment.

Embodiment 4 Assembly and Application of Multienzyme Complex MEC-CIQ

1. Assembly of MEC-CIQ a Multienzyme Complex Containing Four Cellulases (Also Referred to as Cellulose-Hydrolyzing Enzymes)

In this embodiment, the multienzyme complex assembly system MEC-CIQ is applied to the field of artificial cellulosome. Specifically, the selected thermophilic cellulase gene include: (1) a gene of an exoglucanase Ce148S$_{m3}$ obtained by DNA shuffling, (2) a gene of an endoglucanase mutant Cel8A* (K276R, G283P, S329G, S375T) derived from *Clostridium thermocellum*, (3) a gene of an endoglucanase GHSD derived from *Caldicellulosiruptor bescii*, and (4) a gene of a beta-glucosidase CoGH1A derived from *Caldicellulosiruptor owensensis* (each cellulase refers to Matthew A. Smith et al., "A diverse set of family 48 bacterial glycoside hydrolase cellulases created by structure-guided recombination", FEBS Journal, 2012, pages 4453-4465, Vol. 279, No. 24; Michael Anbar et al., "Improved Thermostability of *Clostridium thermocellum* Endoglucanase Cel8A by Using Consensus-Guided Mutagenesis", Applied and Environmental Microbiology, 2012, pages 3458-3464, Vol. 78, No. 9; Igor A. Dvortsova et al., "Carbohydrate binding module CBM28 of endoglucanase Cel5D from *Caldicellulosiruptor bescii* recognizes crystalline cellulose", Int. J. Bio. Macromol, 2017, pages 305-311, Vol. 107; Xiaowei Peng et al., "A multifunctional thermophilic glycoside hydrolase from *Caldicellulosiruptor owensensis* with potential applications in production of biofuels and biochemicals", Biotechnology for Biofuels, 2016, pages 1-13, Vol. 9, No. 98.).

The above four thermophilic cellulase genes are linked with four CL protein genes respectively to form CL-tagged thermophilic cellulases. The specific operation process is as follows.

With the pET28a digested by double enzymes NcoI and XhoI and recovered by agarose gel as the vector skeleton, the four thermophilic cellulase genes are regarded as segments A (A1, A2, A3 and A4), and the four CL protein genes are regarded as segments B (B1, B2, B3 and B4). A and B are connected by Pro/Thr-rich linker sequence (TTVTTPQTS as shown in SEQ ID NO: 17). When designing primers, under the condition that CL-tag is at the N-terminal of cellulase, the reverse primer of B and the forward primer of A contain an overlapping region with a length of 15 bases, the forward primer of B and one end of the NcoI digestion site of the linear vector of contain 15 identical bases, and the reverse primer of A and one end of the XhoI digestion site of the linear vector contain 15 identical bases. In the case of CL-tag at the C-terminal of cellulase, the reverse primer of A and the forward primer of B contain an overlapping region with a length of 15 bases, the forward primer of A and one end of the NcoI digestion site of the linear vector of contain 15 identical bases, and the reverse primer of B and one end of the XhoI digestion site of the linear vector contain 15 identical bases. The PCR products thus obtained has 15 identical bases with the end of the linear vector. The PCR products A and B (e.g., A1 and B1) constitute genes A1-B1 or B1-A1) after the sequence of fragments is determined are transformed into three fragments with the linear vector under the mediation of T5 nuclease exonuclease. After homologous recombination in *Escherichia coli*, genes A, B and the linear vector are assembled into a complete circular plasmid containing CL-tagged thermophilic cellulase genes.

All recombinant vectors of cellulase are expressed by *Escherichia coli* BL21 (DE3) and purified by the Ni-NTA method. The purified protein is assembled with the scaffold protein Scaf-CIQ to form thermostable artificial cellulosome, so as to better hydrolyze cellulose substrate under high-temperature environment. The specific operations are as follows.

Figure 6A:
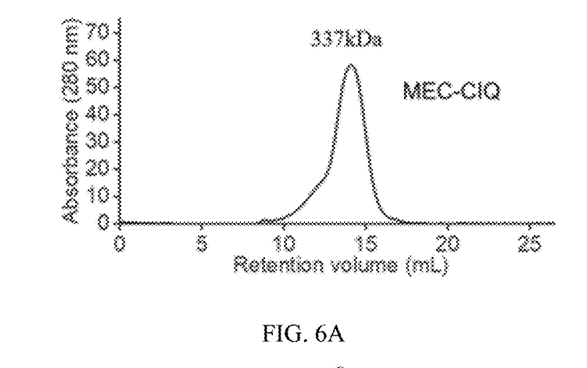
FIGS. 6A-6B illustrate inspection results of the assembly of the multienzyme complex MEC-CIQ equipped with four cellulases according to an embodiment 4 of the disclosure.
Figure 6B:
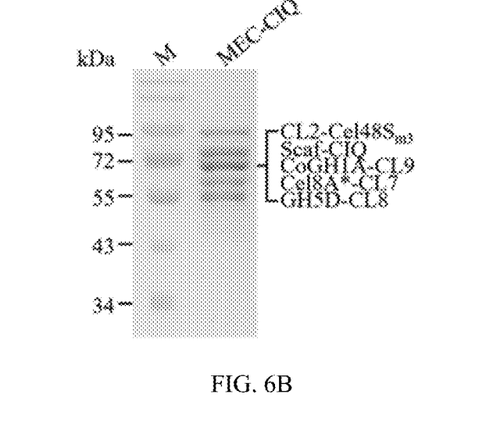

In this embodiment, the system is set as 500 μL, where the final concentration of four CL-tagged cellulases is 3 μM, incubated with equimolar Scaf-CIQ at room temperature for 30 minutes, and subjected to molecular sieve chromatography by AKTA protein purifier. The selected molecular sieve column model is Superose 6 Increase 10/300 GL. TBS buffer is used as purified buffer, and the flow rate is 0.5 mL/min. The assembly of the multienzyme complex is detected according to the peak value and SDS-PAGE, and the detection results are shown in FIGS. 6A-6B. The results show that the molecular sieve results show a single peak, that is, CL2-Ce148S$_{m3}$, Cel8A*-CL7, GH5D-CL8, CoGH1A-CL9 are successfully assembled with the participation of the scaffold protein Scaf-CIQ. The SDS-PAGE results show that the collection peak contains the five expected proteins, and the molecular weight is consistent with the expectation.

2. Synergistic Effect of Four Cellulases in Multienzyme Complex MEC-CIQ

In order to verify the performance of the assembled artificial cellulosome, namely, the multienzyme complex MEC-CIQ containing four cellulases, PASC is used as a cellulose substrate to determine the cellulase activity.

The determination temperature is 65° C., 70° C., 75° C., 80° C., and the reaction time is 3 hours. The final concentration of each cellulase in a 400 μL acetic acid buffer system containing 10 mM CaCl$_2$) is 1 μM and the amount of PASC is 2.5%. The reaction system is centrifuged at 12000 rpm for 1 minute, 120 μL of the supernatant is mixed with 180 μL of DNS solution, and the mixture is treated in a boiling water bath for 10 minutes and then immediately cooled in an ice-water mixture. After centrifugation at 6000 rpm for 1 minute, 250 μL of the reaction solution is collected and the absorbance was measured at OD$_{540}$. The measured values are substituted into the measured glucose standard curve, and the glucose content generated by each group of reactions was calculated. Three groups of independent parallel experiments are set for each group, and four free cellulases without multienzyme complex assembly are used as control.

Figure 7:
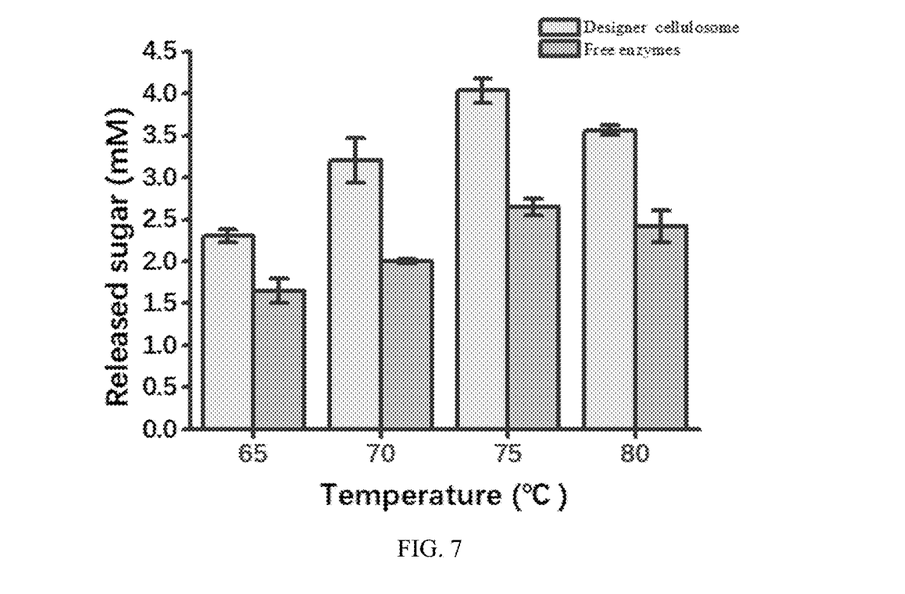
FIG. 7 illustrates detection results of synergistic effects of the four cellulases of the multienzyme complex MEC-CIQ according to the embodiment 4 of the disclosure.

The test results are shown in FIG. 7. The results show that when PASC is used as the substrate, the synergistic effect of multiple enzymes can be demonstrated in each group of experiments. After the MEC-CIQ system reacts at 70° C. for 3 hours, the yield of reducing sugar increases the most, which is 160% of that of free enzyme system. Based on this, the MEC-CIQ system constructed by the disclosure can be successfully applied to the assembly of multienzyme complex, and has excellent performance under high-temperature environment.

The above description is only preferred embodiments of the disclosure, but the scope of protection of the disclosure is not limited thereto. Any change or substitution that can easily be conceived by those skilled in the art within the technical scope disclosed by the disclosure should be included in the scope of protection of the disclosure.

SEQUENCE LISTING

```
Sequence total quantity: 17
SEQ ID NO: 1                    moltype = AA   length = 132
FEATURE                         Location/Qualifiers
source                          1..132
                                mol_type = protein
                                organism = Escherichia coli
SEQUENCE: 1
SKRNKPGKAT GKGKPVGDKW LDDAGKDSGA PIPDRIADKL RDKEFKNFDD FRKKFWEEVS    60
KDPDLSKQFK GSNKTNIQKG KAPFARKKDQ VGGRERFELH HDKPISQDGG VYDMNNIRVT   120
TPKRHIDIHR GK                                                       132

SEQ ID NO: 2                    moltype = AA   length = 131
FEATURE                         Location/Qualifiers
source                          1..131
                                mol_type = protein
                                organism = synthetic construct
SEQUENCE: 2
MSKSNEPGKA TGEGKPVGDK WLDDAGKDSG APIPDRIADK LRDKEFENFD DFRETFWEEV    60
SKDPDLSKQF KGSNKTNIQK GKAPFARKKD QVGGRERFEL NHQKPIEQDG GVYDMNNIRV   120
TTPKRNIDIE G                                                        131

SEQ ID NO: 3                    moltype = AA   length = 88
FEATURE                         Location/Qualifiers
source                          1..88
                                mol_type = protein
                                organism = Escherichia coli
SEQUENCE: 3
MELKHSISDY TEAEFLEFVK KICRAEGATE EDDNKLVREF ERLTEHPDGS DLIYYPRDDR    60
EDSPEGIVKE IKEWRAANGK SGFKQGLE                                       88

SEQ ID NO: 4                    moltype = AA   length = 132
FEATURE                         Location/Qualifiers
source                          1..132
                                mol_type = protein
                                organism = Escherichia coli
SEQUENCE: 4
SKRNKPGKAT GKGKPVNNKW LNNAGKDLGS PVPDRIANKL RDKEFKSFDD FRKKFWEEVS    60
KDPELSKQFS RNNNDRMKVG KAPKTRTQDV SGKRTSFELH HEKPISQNGG VYDMDNISVV   120
TPKRHIDIHR GK                                                       132

SEQ ID NO: 5                    moltype = AA   length = 131
FEATURE                         Location/Qualifiers
source                          1..131
                                mol_type = protein
                                organism = synthetic construct
SEQUENCE: 5
MSKSNEPGKA TGEGKPVNNK WLNNAGKDLG SPVPDRIANK LRDKEFESFD DFRETFWEEV    60
SKDPELSKQF SRNNNDRMKV GKAPKTRTQD VSGKRTSFEL NHQKPIEQNG GVYDMDNISV   120
VTPKRNIDIE G                                                        131

SEQ ID NO: 6                    moltype = AA   length = 87
FEATURE                         Location/Qualifiers
source                          1..87
                                mol_type = protein
                                organism = Escherichia coli
SEQUENCE: 6
MELKNSISDY TEAEFVQLLK EIEKENVAAT DDVLDVLLEH FVKITEHPDG TDLIYYPSDN    60
RDDSPEGIVK EIKEWRAANG KPGFKQG                                        87

SEQ ID NO: 7                    moltype = AA   length = 132
FEATURE                         Location/Qualifiers
source                          1..132
                                mol_type = protein
                                organism = Escherichia coli
SEQUENCE: 7
SKRNKPGKAT GKGKPVGDKW LDDAGKDSGA PIPDRIADKL RDKEFKNFDD FRKKFWEEVS    60
KDPELSKQFN PGNKKRLSQG LAPRARNKDT VGGRRSFELH HDKPISQDGG VYDMDNLRIT   120
TPKRHIDIHR GQ                                                       132

SEQ ID NO: 8                    moltype = AA   length = 131
FEATURE                         Location/Qualifiers
source                          1..131
                                mol_type = protein
                                organism = synthetic construct
SEQUENCE: 8
MSKSNEPGKA TGEGKPVGDK WLDDAGKDSG APIPDRIADK LRDKEFENFD DFRETFWEEV    60
SKDPELSKQF NPGNKKRLSQ GLAPRARNKD TVGGRRSFEL NHQKPIEQDG GVYDMDNLRI   120
TTPKRNIDIE G                                                        131
```

```
SEQ ID NO: 9              moltype = AA  length = 85
FEATURE                   Location/Qualifiers
source                    1..85
                          mol_type = protein
                          organism = Escherichia coli
SEQUENCE: 9
MELKNSISDY TETEFKKIIE DIINCEGDEK KQDDNLEHFI SVTEHPSGSD LIYYPEGNND    60
GSPEAVIKEI KEWRAANGKS GFKQG                                         85

SEQ ID NO: 10             moltype = AA  length = 132
FEATURE                   Location/Qualifiers
source                    1..132
                          mol_type = protein
                          organism = Escherichia coli
SEQUENCE: 10
SKRNKPCKAT GKGKPVGDKW LDDAGKDSGA PIPDRIADKL RDKEFKSFDD FRKAVWEEVS    60
KDPELSKNLN PSNKSSVSKG YSPFTPKNQQ VGGRKVYELH DKPISQGGE VYDMDNIRVT    120
TPKRHIDIHR GK                                                       132

SEQ ID NO: 11             moltype = AA  length = 131
FEATURE                   Location/Qualifiers
source                    1..131
                          mol_type = protein
                          organism = synthetic construct
SEQUENCE: 11
MSKSNEPGKA TGEGKPVGDK WLDDAGKDSG APIPDRIADK LRDKEFESFD DFRETVWEEV    60
SKDPELSKNL NPSNKSSVSK GYSPFTPKNQ QVGGRKVYEL NHQKPIEQGG EVYDMDNIRV    120
TTPKRNIDIE G                                                        131

SEQ ID NO: 12             moltype = AA  length = 86
FEATURE                   Location/Qualifiers
source                    1..86
                          mol_type = protein
                          organism = Escherichia coli
SEQUENCE: 12
MELKHSISDY TEAEFLQLVT TICNADTSSE EELVKLVTHF EEMTEHPSGS DLIYYPKEGD    60
DDSPSGIVNT VKQWRAANGK SGFKQG                                        86

SEQ ID NO: 13             moltype = AA  length = 24
FEATURE                   Location/Qualifiers
source                    1..24
                          mol_type = protein
                          organism = synthetic construct
SEQUENCE: 13
TTTTTTTATT ASSTSTTSTS ATSG                                          24

SEQ ID NO: 14             moltype = AA  length = 18
FEATURE                   Location/Qualifiers
source                    1..18
                          mol_type = protein
                          organism = synthetic construct
SEQUENCE: 14
NTLTIGGGGG GGGTNPGT                                                 18

SEQ ID NO: 15             moltype = AA  length = 27
FEATURE                   Location/Qualifiers
source                    1..27
                          mol_type = protein
                          organism = synthetic construct
SEQUENCE: 15
GASGSGTTTT TTTTTTTTT TGGGTDP                                        27

SEQ ID NO: 16             moltype = AA  length = 25
FEATURE                   Location/Qualifiers
source                    1..25
                          mol_type = protein
                          organism = synthetic construct
SEQUENCE: 16
SSWEGISTDD GIVHSVRISG NKTLS                                         25

SEQ ID NO: 17             moltype = AA  length = 9
FEATURE                   Location/Qualifiers
source                    1..9
                          mol_type = protein
                          organism = synthetic construct
SEQUENCE: 17
TTVTTPQTS                                                           9
```

What is claimed is:

1. A method for preparing a multienzyme complex system, comprising:
   connecting a carbohydrate-binding module 3a (CBM3a), an immunity 2 (Im2) protein, an Im7 protein, an Im8 protein, and an Im9 protein in series through linkers to obtain a scaffold protein;
   forming interaction pairs by connecting a CL2 protein, a CL7 protein, a CL8 protein and a CL9 protein respectively with the Im2 protein, the Im7 protein, the Im8 protein, and the Im9 protein on the scaffold protein;
   connecting target proteins to the CL2 protein, the CL7 protein, the CL8 protein and the CL9 protein respectively to realize an orderly assembly of the target proteins on the scaffold protein, so as to obtain the multienzyme complex system;
   wherein the amino acid sequence of the CL2 protein is shown in SEQ ID NO: 2;
   wherein the amino acid sequence of the CL7 protein is shown in SEQ ID NO: 5;
   wherein the amino acid sequence of the CL8 protein is shown in SEQ ID NO: 8;
   wherein the amino acid sequence of the CL9 protein is shown in SEQ ID NO: 11;
   wherein the amino acid sequence of the Im2 protein is shown in SEQ ID NO: 3;
   wherein the amino acid sequence of the Im7 protein is shown in SEQ ID NO: 6;
   wherein the amino acid sequence of the Im8 protein is shown in SEQ ID NO: 9; and
   wherein the amino acid sequence of the Im9 protein is shown in SEQ ID NO: 12.

2. The method according to claim 1, wherein the CBM3a is derived from *Clostridium thermophilum*.

3. The method according to claim 1, wherein the linkers comprise: a first linker configured to connect between the CBM3a and the Im2 protein, a second linker configured to connect between the Im2 protein and the Im7 protein, a third linker configured to connect between the Im7 protein and the Im8 protein, and a fourth linker configured to connect between the Im8 protein and the Im9 protein;
   wherein the amino acid sequence of the first linker is SEQ ID NO: 13;
   wherein the amino acid sequence of the second linker is SEQ ID NO: 14;
   wherein the amino acid sequence of the third linker is SEQ ID NO: 15; and
   wherein the amino acid sequence of the fourth linker is SEQ ID NO: 16.

* * * * *